(12) United States Patent
Ionescu et al.

(10) Patent No.: US 10,368,794 B2
(45) Date of Patent: Aug. 6, 2019

(54) SYSTEM FOR THE REMOTE MONITORING OF THE HYDRATION STATUS OF A LIVING BEING

(71) Applicant: ECOLE POLYTECHNIQUE FÉDÉRALE DE LAUSANNE (EPFL), Lausanne (CH)

(72) Inventors: Mihai Adrian Ionescu, Ecublens (CH); Hoël Guerin, Lausanne (CH)

(73) Assignee: ECOLE POLYTECHNIQUE FEDERALE DE LAUSANNE (EPFL), Lausanne (CH)

( * ) Notice: Subject to any disclaimer, the term of this patent is extended or adjusted under 35 U.S.C. 154(b) by 448 days.

(21) Appl. No.: 14/840,852

(22) Filed: Aug. 31, 2015

(65) Prior Publication Data
US 2016/0058364 A1 Mar. 3, 2016

(30) Foreign Application Priority Data
Aug. 29, 2014 (WO) .................. PCT/IB2014/064158

(51) Int. Cl.
*A61B 5/00* (2006.01)
*A61B 5/01* (2006.01)
*A61B 5/05* (2006.01)
*A61B 5/07* (2006.01)
(Continued)

(52) U.S. Cl.
CPC ............ *A61B 5/443* (2013.01); *A61B 5/0002* (2013.01); *A61B 5/01* (2013.01); *A61B 5/0507* (2013.01); *A61B 5/0537* (2013.01); *A61B 5/07* (2013.01); *A61B 5/14517* (2013.01); *A61B 5/14546* (2013.01); *A61B 5/6801* (2013.01); *A61B 2560/0214* (2013.01); *A61B 2560/0223* (2013.01); *A61B 2560/0252* (2013.01); *A61B 2562/164* (2013.01)

(58) Field of Classification Search
CPC ..................................................... A61B 5/443
See application file for complete search history.

(56) References Cited

U.S. PATENT DOCUMENTS

| 6,228,385 B1 * | 5/2001 | Shick ................... A61K 8/0208 424/409 |
| 6,591,122 B2 | 7/2003 | Schmitt |

(Continued)

OTHER PUBLICATIONS

A. Caduff, M. S. Talary, and P. Zakharov. 2010. "Cutaneous Blood Perfusion as a Perturbing Factor for Noninvasive Glucose Monitoring." Diabetes Technology & Therapeutics 12 (1): 1-9. doi:10.1089/dia.2009.0095.

(Continued)

*Primary Examiner* — John R Downey
(74) *Attorney, Agent, or Firm* — Nixon & Vanderhye P.C.

(57) ABSTRACT

System for monitoring the hydration status of a living being by exploiting the modulation of backscattered RF electromagnetic waves from a wearable patched placed on the skin, said system comprising:
- a RF-tag adapted to be directly or indirectly fixed to the skin and containing at least one passive integrated circuit coupled to an antenna;
- an electromagnetic RF power source for supplying different signal frequencies to said RF-tag;
- a reader adapted to receive and to process the backscattered electromagnetic waves generated by said electromagnetic power source.

22 Claims, 3 Drawing Sheets

Partial cross section

(51) Int. Cl.
*A61B 5/053* (2006.01)
*A61B 5/145* (2006.01)

(56) References Cited

U.S. PATENT DOCUMENTS

| | | | | |
|---|---|---|---|---|
| 6,849,046 | B1* | 2/2005 | Eyal-Bickels | A61B 5/4869 600/306 |
| 8,734,341 | B2 | 5/2014 | Howell et al. | |
| 2003/0017804 | A1* | 1/2003 | Heinrich | G06K 19/0701 455/41.1 |
| 2005/0070778 | A1* | 3/2005 | Lackey | A61B 5/0537 600/366 |
| 2008/0014142 | A1* | 1/2008 | Dussaud | A61K 49/0006 424/9.1 |
| 2008/0039718 | A1* | 2/2008 | Drinan | A61B 5/05 600/427 |
| 2010/0087899 | A1* | 4/2010 | Erez | A61M 1/0023 607/101 |
| 2012/0116683 | A1* | 5/2012 | Potyrailo | G01N 27/02 702/19 |
| 2012/0166095 | A1* | 6/2012 | Potyrailo | G01N 27/3278 702/23 |
| 2012/0182147 | A1* | 7/2012 | Forster | G06K 19/077 340/572.7 |
| 2013/0123588 | A1 | 5/2013 | Baker, Jr. | |
| 2013/0245388 | A1* | 9/2013 | Rafferty | A61B 5/6831 600/301 |
| 2014/0091811 | A1* | 4/2014 | Potyrailo | G06K 19/0717 324/602 |
| 2014/0095102 | A1* | 4/2014 | Potyrailo | G01R 27/28 702/127 |
| 2015/0025333 | A1* | 1/2015 | Weinstein | A61B 5/02158 600/301 |
| 2015/0378051 | A1* | 12/2015 | Kapoor | G01N 27/02 324/334 |

OTHER PUBLICATIONS

L. Duponchel, S. Laurette, B. Hatirnaz, A. Treizebre, F. Affouard, and B. Bocquet. 2013. "Terahertz Microfluidic Sensor for in Situ Exploration of Hydration Shell of Molecules." Chemometrics and Intelligent Laboratory Systems 123 (April): 28-35. doi:10.1016/j.chemolab.2013.01.009.

K. Finkenzeller, RFID Handbook: Fundamentals and Applications in Contactless Smart Cards and Identification, 2nd ed. New York: John Wiley and Son LTD, 2003.

S. Hajat et al., "Climate change effects on human health: projections of temperature-related mortality for the UK during the 2020s, 2050s and 2080s", J Epidemiol Community Health doi:10.1136/jech-2013-202449.

J. Holstein, F. Canouï-Poitrine, A. Neumann, E. Lepage, and A. Spira, "Were less disabled patients the most affected by 2003 heat wave in nursing homes in Paris, France?," Journal of public health (Oxford, England), vol. 27, No. 4, pp. 359-365, Dec. 2005.

K. Jeong, Y. Huh, S. Kim, Y. Park, J. Son, S. J. Oh, and J. Suh. 2013. "Characterization of Blood Using Terahertz Waves." Journal of Biomedical Optics 18 (10): 107008-107008. doi:10.1117/1.JBO.18.10.107008.

K. Nishihara, W. Iwasaki, M. Nakamura, E. Higurashi, T. Soh, T. Itoh, H. Okada, R. Maeda, and R. Sawada. 2013. "Development of a Wireless Sensor for the Measurement of Chicken Blood Flow Using the Laser Doppler Blood Flow Meter Technique." IEEE Transactions on Biomedical Engineering 60 (6): 1645-53. doi:10.1109/TBME.2013.2241062.

K. Sidler, N. V. Cvetkovic, V. Savu, D. Tsamados and A. M. Ionescu et al. Organic Thin Film Transistors on Flexible Polyimide Substrates Fabricated by Full Wafer Stencil Lithography. XXIII Eurosensors Conference, Lausanne, Switzerland, Sep. 6-9, 2009. Procedia Chemistry.

P.H. Siegel. 2004. "Terahertz Technology in Biology and Medicine." IEEE Transactions on Microwave Theory and Techniques 52 (10): 2438-47. doi:10.1109/TMTT.2004.835916.

* cited by examiner

SYSTEM FOR THE REMOTE MONITORING OF THE HYDRATION STATUS OF A LIVING BEING

CROSS-REFERENCE TO RELATED APPLICATIONS

This application claims the benefit of PCT application No. PCT/IB2014/064158, filed Aug. 29, 2014, the entire content of which is incorporated herein by reference.

FIELD OF THE INVENTION

The present invention relates to the monitoring of the hydration status of a living being. It more precisely relates to the topical monitoring of physiological parameters reflecting the hydration status.

BACKGROUND OF THE INVENTION

Dehydration (hypohydration) is a condition that occurs when the loss of body fluids, mostly water, exceeds the amount that is taken in. More water is moving out of the cells and bodies than what an individual takes in through drinking. With dehydration, the excessive loss of body water is accompanied by disruption of metabolic processes The term dehydration can refer to the following conditions:
  hypernatremia which is defined by an elevated sodium level in the blood (loss/deficit of free water and the attendant "excess" concentration of salt). It is related to a disruption of the body's electrolyte-water balance (osmolarity).
  hypovolemia which is a state of decreased blood volume; more specifically, decrease in volume of blood plasma (loss of blood volume, particularly plasma). The volume loss can be isotonic and preserve the electrolyte-water balance or not (for instance hypotonic state: salt depletion). Hypovolemia is reported to be the most common dehydration form.

Hypernatremia and hypovolemia can co-exist or occur independently; therefore it is important that the measurement principle of the hydration can cover both of them. Particularly, the method used for hydration estimation should be able to quantify the body water loss with an order of magnitude of a few percents variations that reflect different levels of dehydration and different symptoms (see Table below).

| Body water loss | Symptoms | Level of dehydration |
| --- | --- | --- |
| >2% | Threshold: dehydration starting | Minimal |
| >3-4% | Tolerable dehydration, no critical symptoms | Mild |
| >5-8% | Fatigue & dizziness | Moderate |
| >10% | Physical and mental deterioration, severe thirst | Severe |
| >15-25% | Lethal | Very severe |

According to the French National Institute of Health, in 2003 the heat wave in France caused 14'802 heat-related deaths, mostly among the elderly. The number of annual deaths in the UK resulting from the heat is expected to rise by 257% by 2050. The main cause of these worrying figures is acute dehydration.

In sports, dehydration during intense effort and under hot environment conditions leads to reduced performance.

Body mass is often used to assess the rapid changes of hydration in both laboratory and field environments. The level of dehydration is expressed as a percentage of starting body mass. There is evidence that body mass may be a sufficiently stable physiological marker for monitoring daily fluid balance, even over longer periods (1-2 weeks). Over longer periods, changes in body composition (fat and lean mass) are also reflected grossly as changes in body mass, thus limiting this technique for assessment of hydration. This technique is not 100% robust and cannot be used for a real-time assessment of dehydration. Experts acknowledge the difficulty in attempting to assess this true hydration and promote the use of a number of the more established methods to ensure the best representation of hydration status.

There is a stringent demand in terms of wearable systems able to non-invasively evaluate in real time and autonomously the hydration level and the related critical thresholds of a person in various life scenarios.

GENERAL DESCRIPTION OF THE INVENTION

The present invention relates to a wearable system for a topical monitoring of at least one physiological parameter reflecting the hydration status such as skin conductivity, ion concentration in sweat or red blood cell characteristics, said system comprising:
  a RF-tag adapted to be directly or indirectly fixed to the skin and containing at least one passive integrated circuit coupled to an antenna;
  an electromagnetic power source for supplying different signal frequencies to said RF-tag;
  a reader adapted to receive and to process the backscattered electromagnetic waves generated by said electromagnetic power source.

The present invention advantageously offers a remote type of measurement that exploits the influence of the hydration level in the body tissues on some typical characteristics (amplitude and phase) of backscattered electromagnetic waves generated by the electromagnetic source, via the induced impedance change in the antenna when the RF-tag is fixed to the skin.

The RF-tag-antenna sensing works on the principle of mirroring a change in some physical parameter of interest to a controlled change in RF tag electrical properties.

In the present invention sensing is obtained via a tag backscatter power, i.e. for considered transmitted power, an induced mismatch will cause less power to be transmitted to the RF-tag IC for its operations and this appears as a reduced backscatter power response of the tag. This differential backscatter power is used as a sensing mechanism.

The system according to the invention may be advantageously used to non-invasively evaluate in real time the hydration level of a person by a multi-parameter extraction from the backscattering, in the form of radiating electromagnetic waves, of biological tissue.

The incident electromagnetic waves may be supplied externally by a smart hub (smart phone, smart watch or any other personal mobile device) and, after interaction with the RF-tag, the same device detects the backscattered signal and evaluates, based on dedicated signal processing algorithm parameters characterizing the hydration level. The invention can be extended to other applications such as the detection of ions (e.g. sodium, chloride, etc.) or molecules (e.g. glucose, etc.) in skin and sweat, which are known to influence the electrical properties of the sweat and of the skin tissues, therefore being detectable by a changes in the backscattered signals.

The data measured by the passive system are preferably wirelessly collected by the smart hub that can perform more complex signal processing and may serve as interactive display interface with an end-user.

The system according to the invention is capable to detect and perform measurements of electromagnetic waves after they have interacted with the constituents of a biological tissue (typically the skin) that are in close contact with the RF-tag (all acting as an equivalent meta-material with an equivalent impedance depending on the characteristics of the tissues and body fluids) and after they have been backscattered in order to extract multiple parameters. These parameters enable the characterization and extraction of the dehydration level related to both hypernatremia and hypovolemia.

The system according to the invention permits full autonomy and wireless connectivity. It is externally and remotely powered by an electromagnetic radiation emitting device and does not need any energy supply source, which constitutes a considerable advantage compared to any other hydration sensing techniques.

The system according to the invention can be used in combination with existing smart phones or smart watches operating in the range of GHz frequencies but can be extended to other type of remote sensing such as the THz range.

DETAILED DESCRIPTION OF THE INVENTION

The invention will be better understood below with some examples. It should be understood that they are presented to exemplify certain forms of the invention which are not intended to limit the scope of the invention.

In one example of the invention, the passive monitoring tag is powered by an incident wave emitted by a smart hub and comprises a thin flexible substrate (e.g. polyethylene naphthalate, polyethylene terephthalate, polyurethane, polytetrafluoroethylene, paper, polyimide, silicone, etc.) and protective insulating material, one or more antennas to sense signals, in a way adapted to contact human body (skin), and integrated circuit to send backscattered signals to the same mobile hub, and two temperature sensors for sensing both the core-body temperature and the environment temperature. The system is primarily intended to monitor body hydration level but may encompass many other uses.

Figure 1:
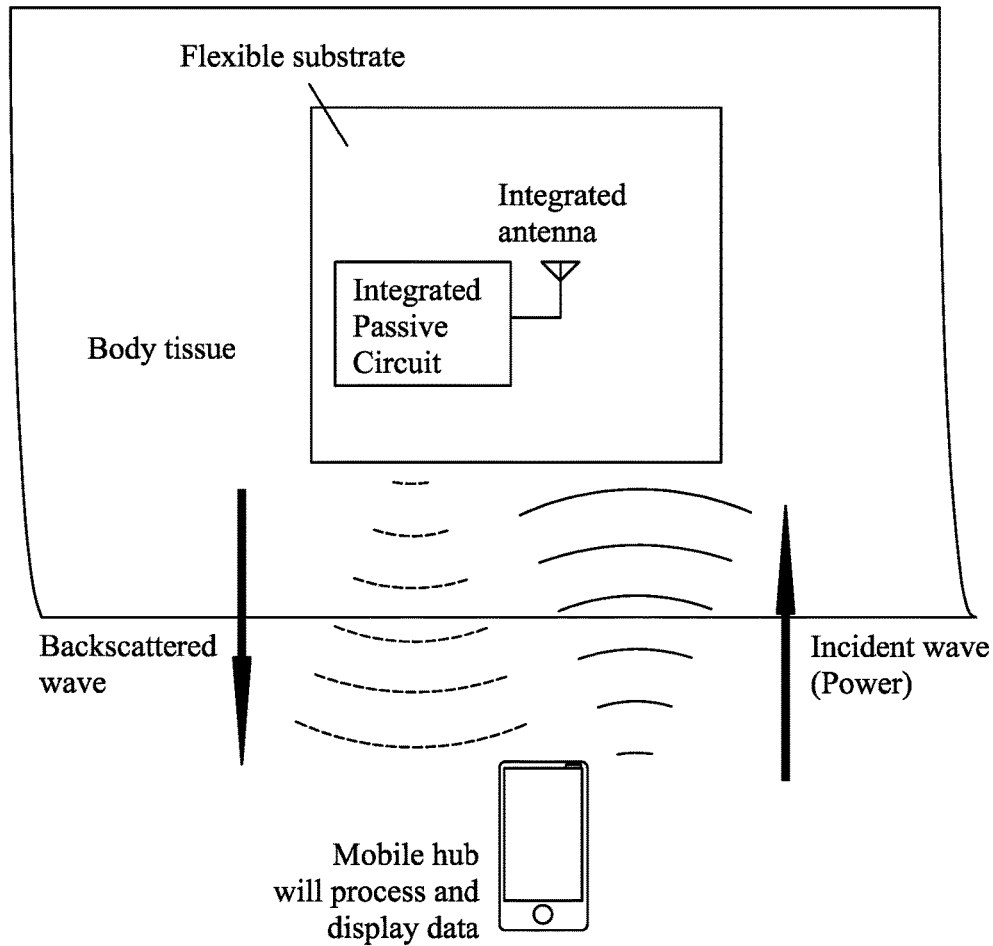
FIG. 1 represents the concept of the invention for determining hydration with a single-site backscattering measurement, multi-parameter extraction and wireless communication to a smart hub (called here mobile device) exploiting: an RF tag placed on the skin, an electromagnetic RF source such as the ones available in mobile phones, an RF reader to detect and evaluate the backscattered signals.

In the example illustrated on FIG. 1 an external smart hub is configured to emit electromagnetic waves at a plurality of frequencies in the low GHz range (implemented in smartphones) at the passive tag in contact with an individual's skin. The backscattered waves are wirelessly sent back to a data acquisition module of the same smart hub. This mobile hub is equipped with dedicated signal processing algorithms to treat the signals, extract physiological parameters such as the water fraction of the tissue, the cardiac output, the red blood cell content and determine the hydration level.

Figure 2:
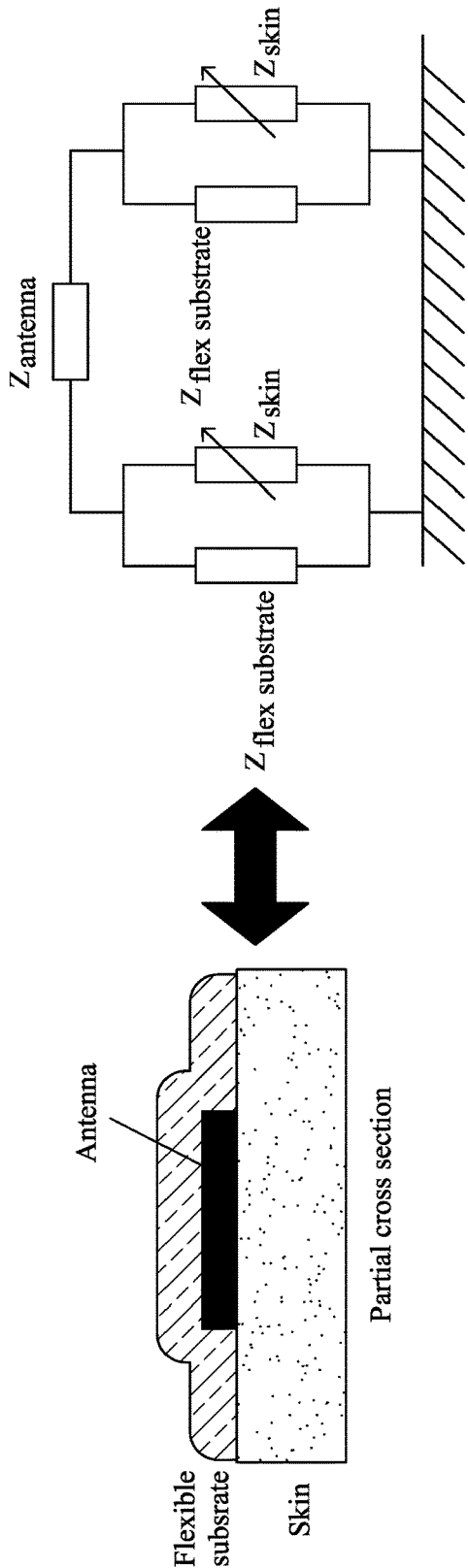
FIG. 2 shows an equivalent circuit of the sensing meta-material composed of a tag flexible substrate, antenna and the skin. The variable impedance of the skin modulates the backscattered wave characteristics which thus carry information on the skin hydration level.
Figure 3:
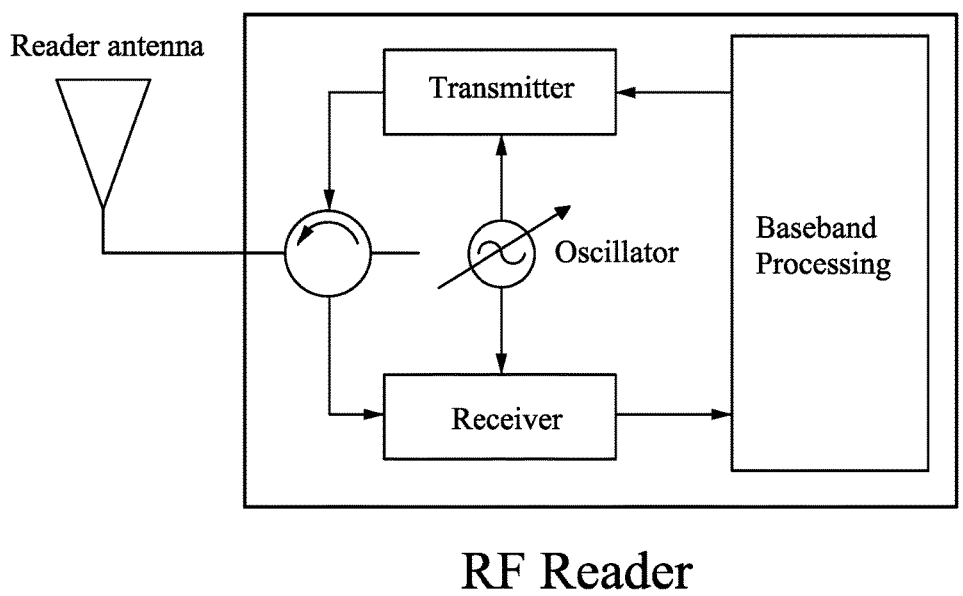
FIG. 3 depicts the RF Reader that includes both the transmitter for the electromagnetic RF sources and the receiver, based on a conventional architecture but with ability to vary the frequency of the electromagnetic wave that is backscattered, according to the method described in this invention.

The extraction of the physiological parameters is made possible by the fact that the backscattered waves sent back by the tag antenna are modulated by the varying electrical properties (e.g. impedance, permittivity) of the skin tissue in contact with the tag. That is to say, the meta-material composed of the tag flexible substrate, antenna and the skin exhibits an equivalent impedance which varies as function of the skin properties that are particularly dependent on its level of hydration (FIG. 2). The loss between the incident and backscattered waves are mainly dominated by the properties of the tissue and they modify the apparent impedance of the passive tag antenna. Permittivity changes, due to the skin tissue dehydration for instance, generate variation of the phase velocity and wavelength of the backscattered radiations. These alterations enable to extract the red blood cell content as well as the cardiac output by Doppler flowmetry for instance. Similarly, at GHz frequencies, the polarization of water molecules in the skin tissue dominates the losses by adsorption of the waves and enables to determine the tissue water content.

A significant part of the invention concerns the use of different signal frequencies that enables to probe at different depth of the skin tissue. Such method scanning different frequencies in the investigation, not only provides access to different tissue layers related losses with a good control of the analyzed depth but also permits to discriminate the most relevant signals from perturbations and noise.

The system according to the invention exploits a backscattering high frequency (MHz, GHz or higher) wave measurement which mirrors the impedance characteristics of a combined flexible patched antenna and of a biological tissue, depending on its hydration level. Externally supplied electromagnetic waves with different signal frequencies in the MHz to GHz range are used and their backscattering characteristics detected and measured. Different modulation schemes available for state-of-the-art tag-to-reader wireless communication can be used. From this measurement, multiple parameters reflecting both hypernatremia and hypovolemia, are extracted therefore levels of any type of body (de)hydration can be quantified.

Such a system can be directly applied on the skin of a person and/or inside some types of garments.

The system is non-invasive and preferably includes a remote RF-tag temperature sensing for accurate calibration on the same substrate.

The system can be made in disposable (such as based on organic electronic or dissolvable materials) and non-disposable (using established and industrially available RF technologies) embodiments. The integration of the antenna can be made on a bio-compatible thin flexible material (such as polyimide) substrate on which metal lines using any type of thin metal layers define the antennas (the use of highly conductive metals or of noble metals such as platinum and gold is preferred for best performance).

The RF-tag is autonomous and does not require any integrated power source. It is powered by the energy coming from the RF waves.

The RF-tag is designed to wirelessly communicate (backscatter radiation from), preferably with a RF Reader integrated in a personal portable hub serving as display interface and offering full local analog-to-digital conversion and digital signal processing capability (running specific algorithms) to extract the information for hydration level but also for other complementary biological parameters characterizing body fluids and skin features.

The invention may be used in different fields, in particular:

First Responder (e.g. Firefighters):

First responders in general and firefighters in particular, are highly exposed to dehydration: the high temperature around them, the physical effort, and the heavy clothing they wear, make them prone to high sweat rates.

Studies have shown that dehydration leads to a loss of alertness, concentration and increased fatigue. This is particularly damaging for professionals who need to react swiftly and remain highly focused.

Athletes:

Studies have shown that as the level of dehydration increases during exercise, various physiological functions are progressively impacted: heart rate and core temperature continually increase over time, while blood volume, stroke volume, cardiac output, and skin blood flow all decrease. For athletes, dehydration is the consequence of the thermal regulation of the body through sweating, which is a mix of water and minerals. In the most intensive effort, the quantity of water lost by the human body can overpass 3.5 liters. In case this loss of water and minerals is not compensated, dehydration can lead to hypovolemia (drop in blood pressure), hypokalemia (paralysis of limbs) and hyponatremia (breathing disorder, disorientation).

These cases are extreme, but what is sure to be a consequence of dehydration is underperforming. Glucose is the gas of the body and glycogen is made of three molecules of water. Thus, without water, an athlete will not be able to use its reserves of glucose. It is estimated that a water loss of 1% to 2% leads to a drop in performance of 10%.

Elderly and Infants:

Fragile segments of the population, like the elderly and infants, are also at risk of dehydration, particularly during extreme heat. The summer 2003 heat wave in France for example caused 14'802 heat-related deaths, mostly among the elderly, according to the French National Institute of Health.[9] Furthermore a recent study predicts that the number of annual deaths in the UK that occur as a result of the heat will rise by 257% by 2050.[10]

REFERENCES

1. T. A. Howell, A. Hadiwidjaja, P. P. Tong, and C. D. Thomas. 2014. "Method and Apparatus to Sense Hydration Level of a Person." U.S. Pat. No. 8,734,341.
2. C. R. Baker. 2013. "Method and Apparatus for Estimating Water Reserves." Patent US20130123588.
3. K. Nishihara, W. Iwasaki, M. Nakamura, E. Higurashi, T. Soh, T. Itoh, H. Okada, R. Maeda, and R. Sawada. 2013. "Development of a Wireless Sensor for the Measurement of Chicken Blood Flow Using the Laser Doppler Blood Flow Meter Technique." IEEE Transactions on Biomedical Engineering 60 (6): 1645-53. doi:10.1109/TBME.2013.2241062.
4. J. M. Schmitt. 2003. "Device and Method for Monitoring Body Fluid and Electrolyte Disorders." U.S. Pat. No. 6,591,122.
5. A. Caduff, M. S. Talary, and P. Zakharov. 2010. "Cutaneous Blood Perfusion as a Perturbing Factor for Noninvasive Glucose Monitoring." Diabetes Technology & Therapeutics 12 (1): 1-9. doi:10.1089/dia.2009.0095.
6. L. Duponchel, S. Laurette, B. Hatirnaz, A. Treizebre, F. Affouard, and B. Bocquet. 2013. "Terahertz Microfluidic Sensor for in Situ Exploration of Hydration Shell of Molecules." Chemometrics and Intelligent Laboratory Systems 123 (April): 28-35. doi:10.1016/j.chemolab.2013.01.009.
7. K. Jeong, Y. Huh, S. Kim, Y. Park, J. Son, S. J. Oh, and J. Suh. 2013. "Characterization of Blood Using Terahertz Waves." Journal of Biomedical Optics 18 (10): 107008-107008. doi:10.1117/1.JBO.18.10.107008.
8. P. H. Siegel. 2004. "Terahertz Technology in Biology and Medicine." IEEE Transactions on Microwave Theory and Techniques 52 (10): 2438-47. doi:10.1109/TMTT.2004.835916
9. J. Holstein, F. Canouï-Poitrine, A. Neumann, E. Lepage, and A. Spira, "Were less disabled patients the most affected by 2003 heat wave in nursing homes in Paris, France?," Journal of public health (Oxford, England), vol. 27, no. 4, pp. 359-65, December 2005.
10. S. Hajat et al., "Climate change effects on human health: projections of temperature-related mortality for the UK during the 2020s, 2050s and 2080s", J Epidemiol Community Health doi:10.1136/jech-2013-202449.
11. K. Finkenzeller, RFID Handbook: Fundamentals and Applications in Contactless Smart Cards and Identification, 2nd ed. New York: John Wiley and Son LTD, 2003.
12. K. Sidler, N. V. Cvetkovic, V. Savu, D. Tsamados and A. M. Ionescu et al. Organic Thin Film Transistors on Flexible Polyimide Substrates Fabricated by Full Wafer Stencil Lithography. XXIII Eurosensors Conference, Lausanne, Switzerland, Sep. 6-9, 2009, Procedia Chemistry.

The invention claimed is:

1. A wearable system for topically monitoring a physiological parameter reflecting a hydration status of a body of a living being, the system comprising:
    a RF-tag adapted to be directly or indirectly fixed to the skin of the living being and including a passive integrated circuit coupled to an antenna;
    an electromagnetic RF power source for supplying an incident wave having different signal frequencies to the RF-tag;
    a RF reader adapted to receive and to process backscattered electromagnetic waves that are backscattered by the RF-tag based on the incident wave generated by the electromagnetic RF power source to measure a variable impedance of the skin, and
    a data processor for determining a hydration level of the body of the living being based on measured variable impedance to determine whether the body of the living being is dehydrated.

2. The system according to claim 1 further comprising:
    a sensor for measuring the environment temperature; and
    a sensor for measuring at least one of the skin and the core-body temperature to provide for at least one of calibrated measurements taking into account a temperature influence on impedance characteristics, and independent monitoring of skin and/or core-body temperature.

3. The system according to claim 1, comprising a flexible substrate connected to the RF-tag adapted to be fixed to the skin.

4. The system according to claim 1 wherein the power source and the reader are included in a same element.

5. A method for monitoring a hydration status of a body of a living being with a wearable system, the wearable system including a RF-tag having a passive integrated circuit coupled to an antenna, an electromagnetic RF power source, and a RF reader adapted to receive and to process backscattered electromagnetic waves backscattered by the RF-tag, the method comprising the following steps:

directly or indirectly fixing the RF-tag to a skin of the living being;

generating towards the RF-tag an incident wave having different signal frequencies with the RF power source to cause the backscattered electromagnetic waves from the RF-tag;

collecting and processing the backscattered electromagnetic waves by the RF reader generated by the power source to determine a variable impedance of the skin, and determining a hydration level of the body to determine whether the body of the living being is dehydrated by processing the measured variable impedance.

6. The method according to claim 5 further comprising the step of:

determining ions, bio-markers and other molecules, in at least one of the skin, and the sweat of the living being based on the backscattered electromagnetic waves.

7. The system according to claim 1, wherein the passive integrated circuit of the RF-tag is configured to be powered by energy coming from the incident wave supplied by the electromagnetic RF power source.

8. The system according to claim 1, wherein the RF-tag is configured to modulate wave characteristics of the backscattered electromagnetic waves based on an impedance characteristic of the antenna and a biological tissue at the skin.

9. The system according to claim 1, wherein the passive integrated circuit of the RF-tag is configured to send the backscattered electromagnetic waves to the RF reader via the antenna.

10. The system according to claim 1, wherein the backscattered electromagnetic waves include hydration information of the skin.

11. The method according to claim 5, further comprising the step of:

powering the passive integrated circuit of the RF-tag by energy coming from the incident wave generated by the electromagnetic RF power source.

12. The method according to claim 5, wherein in the step of generating, the RF-tag modulates wave characteristics of the backscattered electromagnetic waves based on an impedance characteristic of the antenna and a biological tissue at the skin.

13. The method according to claim 5, wherein in the step of generating, the passive integrated circuit of the RF-tag sends the backscattered electromagnetic waves to the RF reader via the antenna.

14. The method according to claim 5, wherein the backscattered electromagnetic waves include hydration information of the skin.

15. The system according to claim 1, wherein the hydration level of the body is determined based on a variation of a phase velocity and a wavelength of the backscattered electromagnetic waves.

16. The method according to claim 5, wherein the hydration level of the body is determined based on a variation of a phase velocity and a wavelength of the backscattered electromagnetic waves.

17. The system according to claim 1, wherein the different signal frequencies are used to probe at different depths of the skin tissue to determine the hydration level.

18. The method according to claim 5, wherein the different signal frequencies are used to probe at different depths of the skin tissue to determine the hydration level.

19. The system according to claim 1, wherein the hydration level of the body is determined based on an amplitude and a phase of the backscattered electromagnetic waves.

20. The method according to claim 5, wherein the hydration level of the body is determined based on an amplitude and a phase of the backscattered electromagnetic waves.

21. The system according to claim 1, wherein the determination whether the body of the living being is dehydrated includes a determination whether hypernatremia and hypovolemia of the body is present.

22. The method according to claim 5, wherein the step of determining the hydration level includes a determination whether hypernatremia and hypovolemia of the body is present.

* * * * *